United States Patent [19]

Brook

[11] Patent Number: 4,842,597

[45] Date of Patent: Jun. 27, 1989

[54] HYDROPHILIC COPOLYMERS FOR WOUND DRESSINGS AND OTHER BIOMEDICAL USES

[75] Inventor: Michael G. Brook, Chessington, England

[73] Assignee: Fulmer Yarsley Ltd., Surrey, England

[21] Appl. No.: 50,019

[22] Filed: May 15, 1987

[30] Foreign Application Priority Data

May 15, 1986 [GB] United Kingdom ............... 8611838

[51] Int. Cl.$^4$ ...................... A61F 13/18; A61L 15/00
[52] U.S. Cl. .................................. 604/368; 604/372; 128/156
[58] Field of Search .................... 623/11; 128/156; 604/368, 372, 376

[56] References Cited

U.S. PATENT DOCUMENTS

| | | | |
|---|---|---|---|
| 3,686,024 | 8/1972 | Nankee | 604/368 |
| 3,901,810 | 8/1975 | Brooks et al. | 210/500.28 |
| 3,929,741 | 12/1975 | Laskey | 521/38 |
| 3,932,602 | 1/1976 | Sweger | 424/45 |
| 4,136,250 | 1/1979 | Mueller et al. | 525/474 |
| 4,192,727 | 3/1980 | Ward | 604/368 |
| 4,300,820 | 11/1981 | Shah | 525/205 |
| 4,486,489 | 12/1984 | George | 604/372 |
| 4,526,909 | 7/1985 | Urist | 623/11 |
| 4,693,776 | 9/1987 | Krampe et al. | 128/156 |
| 4,732,808 | 3/1988 | Krampe et al. | 128/156 |
| 4,743,244 | 5/1988 | Le Khac | 128/156 |

*Primary Examiner*—Stephen C. Pellegrino
*Assistant Examiner*—Sharon Rose
*Attorney, Agent, or Firm*—Burns, Doane, Swecker & Mathis

[57] ABSTRACT

A hydrophilic article is disclosed which is a layer of a non-cross-linked copolymer of a hydrophobic monomer component and a hydrophilic monomer component. Preferred hydrophobic monomers are lower alkyl esters of methacrylic and acrylic acids and preferred hydrophilic monomers are vinyl pyrrolidone and hydroxy ethyl methacrylates. The hydrophilic articles of the invention are useful in biomedical applications, especially in wound dressings and as coatings on catheters.

9 Claims, 1 Drawing Sheet

HYDROPHILIC COPOLYMERS FOR WOUND DRESSINGS AND OTHER BIOMEDICAL USES

BACKGROUND OF THE INVENTION

This invention relates to hydrogels of copolymers which are useful in the preparation of materials which are applied to body tissues, such as wound dressings.

Hydrogels are polymeric materials capable of retaining substantial quantities of absorbed water. Typically, cross-linked hydrophilic polymers can be prepared which absorb between half to five times their own weight to yield elastic solids. In the dry state, (in which they are sometimes described as Xerogels), the hydrophilic polymers are generally hard and rigid; in the hydrated state softer and elastic. The precise properties depend on the composition and the structure of the hydrogel and the amount of water absorbed. They are not soluble in water but swollen by it in a predictable manner.

Until now hydrogels have been made by crosslinking hydrophilic polymers. The crosslinks hold the molecules together and give it mechanical integrity, while the absorbed water acts as a plasticiser for the sections of hydrophilic polymer between the crosslinks, giving them mobility relative to each other. The hydrated hydrogel, therefore, behaves in a similar way to vulcanized natural rubber.

Cross-linking has generally been effected by incorporating a bi- or polyfunctional unsaturated monomer in the monomer mixture from which the hydrophilic copolymer is prepared. One of the most commonly used hydrophilic monomers which has been used for preparation of hydrogels is hydroxyethyl methacrylate (HEMA). Commercially available HEMA contains quantities of dimethylacrylates as impurities so that its polymers are generally cross-linked. Another method which has been used to effect cross-linking of hydrophilic polymers is by irradiation of a solution of the polymer with gamma or X-rays or an electron beam.

Hydrophilic polymers have been used to prepare articles which come into contact with body tissue, such as contact lenses and surgical implants in which their biocompatability has been exploited.

European patent application No. 0107376 (Johnson & Johnson Products Inc.) discloses a wound dressing which is based on a transparent layer of a water-swollen cross-linked homopolymer of N-vinyl pyrrolidone (VP). The homopolymer of VP is first prepared and dissolved in water. A hydrogel layer is then formed by irradiating with gamma rays while contained within a polythene bag.

Chemical Abstracts, Vol 89, 1978, page 376 (Hidekatsu et al), also discloses a similar wound dressing which consists of a homopolymer of N-vinyl pyrrolidone or of vinyl alcohol which has been cross-linked by gamma irradiation of the homopolymer while retained between glass plates.

Cross-linked polymers have the disadvantages that they cannot be moulded or extruded from a melt or cast from a solution of the polymer and this limits the applications to which hydrophilic polymers can be put.

SUMMARY OF THE INVENTION

According to one aspect of the present invention, there is provided a hydrophilic article for use in contact with body tissue which comprises a layer of an essentially un-cross-linked copolymer and hydrophobic monomer components and hydrophilic monomer components, wherein the hydrophobic monomer is selected from at least one ester of an unsaturated acid of the general formula $CH_2=CRCOOR^1$, where R is hydrogen or $CH_3$ and $R^1$ is a linear or branched chain alkyl group and wherein the hydrophilic component is selected from the group of monomers consisting of N-vinyl pyrrolidone, acrylic or methacrylic acid and esters of acrylic or methacrylic acid of the general formula $CH_2=CRCOOR^2$, where R is hydrogen or $CH_3$ and $R^2$ is an hydroxy-terminated alkyl or alkoxy group.

Despite the absence of cross-linking, the hydrophilic copolymers prepared in accordance with this invention are able to absorb and retain substantial quantities of water. The amount of water uptake depends on the amount and nature of the hydrophilic component.

Water uptakes may be as high as 590% of the dry weight of the copolymer material and typically are in the region of 180 to 250. In the context of this specification, water uptake is defined as:

$$= \frac{\text{wt. of hydrated material} - \text{wt. of dry material}}{\text{wt. of dry material}} \times 100$$

It is also convenient to define the degree of hydration of the resulting hydrogels in terms of their equilibrium water content (EWC), where $$EWC = \frac{\text{wt. of hydrated material} - \text{wt. of dry material}}{\text{wt. of hydrated material}} \times 100$$

The hydrophobic component may comprise, for example, methyl or ethyl acrylate or methacrylate. Typical hydrophilic monomers are vinyl pyrrolidone, hydroxyethyl acrylate or methacrylate and hydroxy propyl methacrylate.

Preferred hydrophilic monomers are vinyl pyrrolidone (VP) and hydroxyethyl methacrylate (HEMA). As mentioned above, commercial grades of HEMA contain significant quantities of dimethacrylate monomers as impurities. Although these may be removed by fractional distillation it is preferable to avoid this operation. Thus, if a low degree of cross-linking is desired in the copolymers it is preferable to use at most only minor proportions of HEMA in the polymerisation mixtures.

One particular practical application of the hydrophiliccopolymers of the invention is in wound dressing.

According to a further aspect therefore, the invention provides a wound dressing which comprises a flexible layer of a hydrogel formed from an essentially un-cross-linked copolymer of hydrophobic monomer components and hydrophilic monomer components, the hydrophobic components being selected from one or more esters of acrylic or methacrylic acid of the general formula $CH_2=CRCOOR^1$, where R is hydrogen or $CH_3$ and $R^1$ is a linear or a branched chain alkyl group and the hydrophilic components being selected from one or more of the following monomers; N-vinyl pyrrolidone, acrylic or methacrylic acid, and esters of acrylic or methacrylic acid of the general formula $CH_2=CROOR^2$, where R is hydrogen or $CH_3$ and $R^2$ is a hydroxyl terminated alkyl or alkoxy group.

The hydrophilic nature of the copolymers depends, inter alia, on the selection of the particular hydrophobic and hydrophilic comonomers and the proportions in which they are copolymerised. Increase in the molar proportion of the hydrophilic component will result in a copolymer having a higher capacity for water absorption and accordingly a resultant hydrogel having a higher water content. In general, we aim to produce a copolymer which is capable of absorbing at least 180%, preferably at least 200% of its weight of water.

In the case of copolymers which are based on methyl methacrylate (MMA) as the hydrophobic monomer, and vinyl pyrrolidone (VP) as the hydrophilic monomer, a copolymer formed from about 2 moles of VP and one mole of MMA will generally be capable of absorbing about 200% of its weight of water. On the other hand, a decrease in the proportion of the hydrophobic component reduces the mechanical strength of the hydrogel. This is not, however, a serious limitation in the freedom to produce hydrogels having very high equilibrium water contents approaching 80 to 90% of the weight of the hydrated copolymer since the hydrogel layer can be reinforced with a fabric or film or deposited on a plastics substrate for many biomedical applications. It is therefore feasible to utilise copolymers which contain as much as 4 to 5 moles of hydrophilic monomer per mole of phydrophobic monomer. In any event, the mechanical strength of hydrogels prepared in accordance with the invention compares favourably with the equivalent properties of gels produced by gamma radiation or electron beam-induced cross-linking of PVP solutions.

The use of un-cross-linked hydrophilic copolymers in the formation of the hydrogel layers in accordance with this invention has an important manufacturing advantage since the hydrogel layer can be cast directly from a solution containing the copolymer or be formed into any desired shape by traditional plastics moulding techniques, e.g. injection moulding and extrusion.

For example, a copolymer of MMA and VP may be prepared by solution polymerisation using sufficient solvent, which is preferably water-miscible (e.g. an alcohol) for the MMA & VP to maintain the monomers in solution. It is advantageous to include a minor amount of water, e.g. about 20% by volume of the solvent, in order to cause some hydration of the resulting copolymer. The resulting copolymer solution may be cast on a suitable substrate to form, after removal of the co-solvent, e.g. by evaporation, a hydrophilic layer which can be swollen or swollen further by application of water or an aqueous medium. In order to maintain the polymerisation reaction at a reasonable rate, it may be necessary to heat the polymerisation mixture to a temperature in the range of about 50° to 90°. The substrate on which the polymer layer is cast may have a release surface or include a film or fabric which is bonded to and becomes part of the ultimate wound dressing or other biomedical article.

Preferably, the hydrophilic copolymers are prepared by dispersion polymerisation in a non-aqueous continuous phase. Polymerisation is effected in the presence of a graft dispersant precursor which prevents coalescence of the growing polymer particles. Also, this method enables a monogeneous copolymer (which has greater transparency and clarity) to be parepared since the monomers can be added to the reaction mixture during the course of the polymerisation in amounts which compensate for their different reactivities.

The hydrogel layer may be reinforced with a fabric or film especially when used as a wound dressing. A nonwoven fabric is preferred, e.g. a scrim formed by crossbonding of polyolefin fibres. It is also possible as an alternative or in addition to reinforce the layers with a polymer film, which is permeable to gases and water vapour, examples being cellulose and ethylene vinyl acetate films.

Wound dressings prepared in accordance with the invention may include a protective film which is stripped off before application of the dressing to the wound. Such protective films preferably have a release surface to ensure easy stripping from the gel layer. Examples include polyethylene and polysiloxane coated films.

An advantage of the wound dressings of this invention compared with many conventional dressings is that the hydrogel layer is generally transparent so that the progress of the healing of the wound can be monitored without removing the dressing. Also, because of the absorbent nature of the hydrogel, chemotherapeutic substances, such as anti-bacterial compounds can be dissolved in the aqueous component of the gel, from which they are slowly released into the vicintiy of the wound.

The high water content hydrogels produced in accordance with this invention have a highly flexible nature which enables them to conform to the wound area when used as dressings. Also, hydrogels having a large molar proportion of the hydrophilic comonomer may have a slight surface tack which facilitates location and attachment of the dressing to a wound area.

The following Examples illustrate the preparation of copolymers in accordance with the invention:

Examples 1 to 8

A number of monomer mixtures containing MMA and VP, with or without HEMA, in various proportions were prepared. About 1% by weight of azo-diisobutyronitrile was added to each composition as the polymerisation initiator and nitrogen was bubbled through the monomer mixtures to mix the catalyst thoroughly into the monomers, remove oxygen dissolved in the monomers and to provide an inert atmosphere. Each sample monomer mixture was heated to 30° C. in a polythene tube for 24 hours, raised to 60° C. for 2 hours and then 90° C. for two hours before allowing the resulting polymers to cool to room temperature. The polymers were then removed from the tubes and their water absorption tested.

The results are as follows:

| Example No. | Molar Ratios | | | % Water up-take |
| --- | --- | --- | --- | --- |
| | MMA | HEMA | VP | |
| 1 | 1 | — | 2 | 228 |
| 2 | 1 | — | 1 | 94 |
| 3 | 1 | 1 | 2 | 149 |
| 4 | 1 | 2 | 1 | 43 |
| 5 | 1 | 2 | 2 | 115 |
| 6 | 1 | 1 | 1.5 | 95 |
| 7 | 4 | 2 | 4.5 | 86 |
| 8 | 1 | — | 4 | 590 |

In all cases the polymers when hydrated were transparent, flexible soft materials.

Example 9 (Best mode)

A mixture of methyl methacrylate (0.5 g), vinyl pyrrolidone (6.2 g), a graft dispersant precursor (4.0 g) based on polylauryl methacrylate (prepared by the method described on page 107 of "Dispersion Polymerisation in Organic Media", edited by K. E. J. Barrett and published by Wiley), azo-diisobutyronitrile (0.09 g) and petroleum spirit boiling range 60°–80° C., (240 g) was prepared in a flask fitted with a mechanical stirrer, a nitrogen inlet, a non-reflux condenser and the means for returning cold condensed distillate to the flask. After flushing the mixture and the apparatus with oxygen-free nitrogen, the stirred mixture was heated by means of a water bath so that about 3ml/minute of distillate was condensed and returned to the flask. An oxygen-free atmosphere was maintained throughout the apparatus at all times. After the mixture had boiled for 1 hour, a further mixture of methyl methacrylate (0.5 g), vinyl pyrrolidone (6.5 g), graft dispersant precursor (2.0 g) and azodiisobutyronitrile (0.02 g) was added at a rate of 0.3 ml every 3 minutes into the stream of cold distillate returning to the flask. When addition of this mixture was complete, a futher mixture of methyl methacylate (12.95 g) vinyl pyrrolidone (8.30 g) and azodiisobutyronitrile (0.09 g) was added in the same way. The rate of addition was increased to 0.7m½ minutes, 3 hours after the making of additions began. After the completion of additions, the mixture was boiled gently for four hours and allowed to cool under nitrogen. Stirring was then discontinued. A white mixture was obtained which was a dispersion of particles of copolymer in petroleum spirit. Drying gave a free-flowing fine powder which may be melt-processed or dissolved in a suitable solvent such as industrual methylated spirits and cast as a thin film.

In another experiment, the solid, powdered polymer of Example 9 was placed on the base of a preheated steel mould of a hydraulic press and held under a pressure of 2000 psi for 10 minutes at 150° to 170° C. A transparent, slightly brittle moulding about 2 mm thick was produced, which was transformed in a soft, flexible transparent sheet when swollen in water for 24 hours. When applied to the skin, the hydrogel layer adhered slightly and could be held in place with a gauze strip.

Increasing the VP content of the polymers tends to produce hydrogels which are softer and slightly tacky and this may be advantageous, especially where the hydrogel layer is supported on a reinforcing film or fabric.

In cases where acrylic and/or methacrylic acid are included in the copolymerisation mixture, the resulting copolymer will have free carboxylic acid groups. These carboxylic acid groups can be converted to various derivatives, e.g. by post treatment with an alkaline solution to impart some ionic character to the copolymer. The presence of free carboxylic acid groups may also be advantageous for bonding of chemotherapeutic agents. Other kinds of ionic groups may be incorporated into the copolymers, e.g. the inclusion of a proportion of acrylamide or methacrylamide into the monomer mixture will result in amide groups being present in the resultant copolymer.

The hydrophilic copolymers of this invention have other advantageous biomedical uses. For example, the copolymers may be coated onto catheters or catheter tips to render them more biocompatible and to reduce the likelihood of blood clots forming on the catheter surface. Catheters are conventionally formed by extrusion from p.v.c. A coating of a hydrogel can be formed on the outer surface of the catheter by dipping the catheter in a solution of the hydrophilic copolymer and the solvent evaporated. The hydrophilic copolymers may be dissolved in a solvent such as ethanol, tetrahydrofuran or 2-ethoxyethanol. Because the solubility of the copolymers is relatively low in these solvents, a thin coating about 1 to 10 μm will be formed after evaporation of the solvent. The resulting coating may thereafter be hydrated to produce an adherent, biocompatible, lowfriction surface which facilitates the insertion of the catheter through skin into blood vessels or along other body passages. The latter purpose is particularly relevant to catheters used in the treatment and monitoring of new born babies. It is also possible to apply the hydrophilic copolymer layer to the outer surface of the catheter by co-extrusion.

A more specialised application of the hydrophilic polymers is for coating urinary catheters for female geriatric patients. Because of the loss of muscle action these patients exhibit, conventional catheters tend to leak or fall out. Very large diameter catheters might be satisfactory but nursing staff are reluctant to use them. A catheter which expands after insertion can be made by applying a thick coating of a high water absorption hydrogel. In this case, a layer of hydrophilic copolymer is coextruded as the outer surface of the catheter. The resulting catheter is partially hydrated before the catheter is inserted to make it flexible and would then swell further after insertion to seal and retain the catheter. Alternatively or additionally, the copolymer layer could form a collar of hydrogel near one end of the catheter in the region of the tip.

Hydrophilic polymers prepared in accordance with this invention may also be used for other medical and dental purposes. For example, the polymers may be foamed to produce hydrophilic foamed mouldings which can be used in devices to collect urine such as urostomy bags and absorbent pads. Conveniently, the anhydrous polymers are mixed to powder form with a blowing agent and then subjected to injection moulding to produce moulded foams of the desired shape. Such foams have an extremely high affinity for water.

Another application of the anhydrous polymers is in sealing plugs or posts in the teeth. In this application, the polymer is coated onto the plug or post before they are inserted. In the presence of saliva, the polymers will swell to seal the gap between plug or post and the tooth and exclude the ingress of foreign material.

BRIEF DESCRIPTION OF THE DRAWING

The accompanying FIGURE shows a urinary catheter coated with a partially hydrated copolymer layer in accordance with the invention.

DETAILED DESCRIPTION OF THE DRAWING

Figure 1:
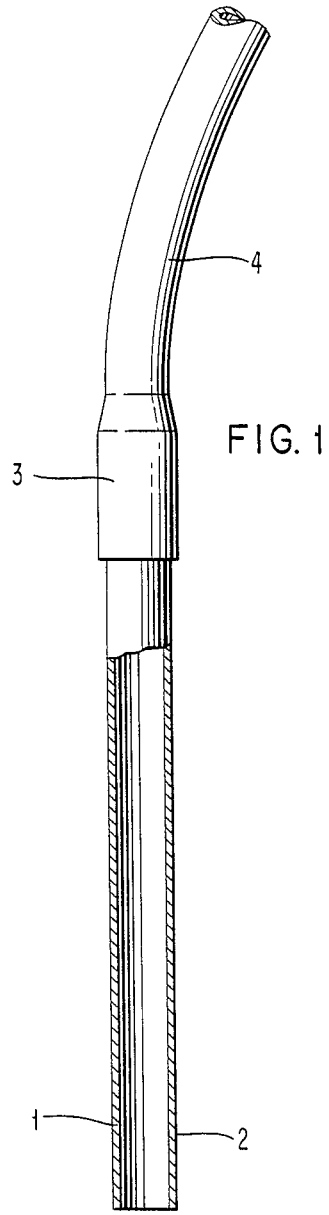
Figure 2:
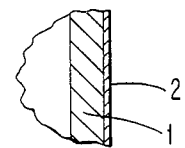

The catheter comprises a tube 1 of plasticised p.v.c. (shown in section). A layer of a hydrophilic copolymer 2 has been co-extruded onto the outer surface of the tube 1. The catheter includes a connector 3 and a flexible tube 4 for connecting the catheter to a suitable collecting bag.

I claim:

1. A wound dressing comprising a hydrogel layer having a water content of at least 50% by weight, said hydrogel consisting essentially of a water-swollen, substantially uncross-linked hydrophilic copolymer of a hydrophobic monomer component and a hydrophilic monomer component, wherein the hydrophobic monomer component comprises a lower alkyl acrylate or methacrylate ester and the hydrophilic monomer component is selected from N-vinyl pyrrolidone (NVP), and mixtures of NVP and one or more hydroxy alkyl acrylate and methacrylate, the hydrophobic and hydrophilic monomer components being copolymerized in the molar ratio of from 1:1 to 1:4.

2. A wound dressing according to claim 1 in which the copolymer is capable of absorbing at least about 200% by weight of water.

3. A wound dressing according to claim 1 which includes a protective film covering the hydrogel layer, said film being strippable from the hydrogel layer.

4. A wound dressing according to claim 1 in which the copolymer is prepared by subjecting the monomers to non-aqueous dispersion polymerization in the presence of a graft dispersant precursor which stabilizes the dispersion of polymer particles.

5. A wound dressing according to claim 1 in which the hydrogel layer includes a chemotherapeutic substance dissolved in the aqueous compound of the hydrogel.

6. A wound dressing according to claim 1 wherein the hydrophobic component is methyl methacrylate and the hydrophilic component is vinyl pyrrolidone with or without hydroxy ethyl methacrylate.

7. A wound dressing according to claim 1 and in which the copolymer is capable of absorbing at least about 180% by weight of water.

8. A wound dressing according to claim 1 wherein the copolymer is prepared by copolymerising methyl methacrylate and vinyl pyrrolidone in the molar proportions of from about 1:1 to about 1:4.

9. A wound dressing according to claim 1 in which the hydrogel layer is supported by a reinforcing film or fabric.

* * * * *